United States Patent
Zhong et al.

(10) Patent No.: US 11,406,100 B2
(45) Date of Patent: Aug. 9, 2022

(54) ACELLULAR COLLAGENOUS TISSUE AND A PROCESSING METHOD OF ARTIFICIAL HEART VALVE COMPRISING THE ACELLULAR COLLAGENOUS TISSUE

(71) Applicant: KINGSTRONBIO (CHANGSHU) CO., LTD., Changshu (CN)

(72) Inventors: Shengping Sam Zhong, Changshu (CN); Jing Liu, Changshu (CN)

( * ) Notice: Subject to any disclaimer, the term of this patent is extended or adjusted under 35 U.S.C. 154(b) by 0 days.

(21) Appl. No.: 15/275,322

(22) Filed: Sep. 23, 2016

(65) Prior Publication Data
US 2017/0006858 A1 Jan. 12, 2017

Related U.S. Application Data

(63) Continuation of application No. PCT/CN2015/074975, filed on Mar. 24, 2015, which is a continuation of application No. PCT/CN2014/073969, filed on Mar. 24, 2014.

(51) Int. Cl.
*A01N 1/02* (2006.01)
*A61F 2/24* (2006.01)

(52) U.S. Cl.
CPC .......... *A01N 1/021* (2013.01); *A01N 1/0215* (2013.01); *A61F 2/2415* (2013.01); *A61F 2/2427* (2013.01); *A61F 2220/0075* (2013.01)

(58) Field of Classification Search
None
See application file for complete search history.

(56) References Cited

U.S. PATENT DOCUMENTS

| | | | |
|---|---|---|---|
| 8,007,992 B2* | 8/2011 | Tian | A61L 27/3604 435/1.1 |
| 8,361,144 B2* | 1/2013 | Fish | A61F 2/0095 623/2.11 |
| 9,696,247 B2* | 7/2017 | Goldsborough | G01N 1/30 |
| 2006/0241287 A1 | 10/2006 | Hecht et al. | 530/356 |

OTHER PUBLICATIONS

Yang Hu et al. "Evaluation of 1-ethyl-3-methylimidazolium acetate based ionic liquid systems as a suitable solvent for collagen". Journal of Applied Polymer Science (2013), 130(4), 2245-2256.*
Majewski et al. "Ionic liquids in embalming and tissues preservation". Acta Histochemica. 2003, 105(2), pp. 135-142.*
The extended European Search Report of corresponding European application No. 15767882.2-1454/3123860, dated Sep. 27, 2017.

* cited by examiner

Primary Examiner — Vera Afremova

(57) ABSTRACT

The present invention provides a decellularized collagenous tissue and a method for processing an artificial heart valve containing the decellularized collagenous tissue. The method comprises immersing the decellularized collagenous tissue in a preservation liquid containing an ionic liquid until the size of the decellularized collagenous tissue remains stable in a non-liquid environment. The present invention also provides a preservation method, comprising immersing the decellularized collagenous tissue or the artificial heart valve containing decellularized collagenous tissue in the preservation liquid containing ionic liquid until the size of the collagen tissue remains stable in the non-liquid environment. The present invention also provides a decellularized collagenous tissue and an artificial heart valve containing the decellularized collagenous tissue processed by the method described above. The method can effectively avoid a biological material damage caused by being in a non-liquid environment and is beneficial to implement a subsequent processing and sterilization for the biological material.

4 Claims, No Drawings

ACELLULAR COLLAGENOUS TISSUE AND A PROCESSING METHOD OF ARTIFICIAL HEART VALVE COMPRISING THE ACELLULAR COLLAGENOUS TISSUE

CROSS-REFERENCE TO RELATED APPLICATIONS

This application is a continuation of International Application No. PCT/CN2015/074975, filed on Mar. 24, 2015, which claims priority to an International Application No. PCT/CN2014/073969, filed on Mar. 24, 2014, which is hereby incorporated by reference in its entirety.

FIELD OF THE TECHNOLOGY

The present invention relates to a decellularized collagenous tissue and a processing method of an artificial heart valve comprising the decellularized collagenous tissue, which belong to the technical field of medical device.

BACKGROUND

Many biological materials, especially biological materials derived from natural tissue, and medical device, in order to maintain their performance, are often required to be preserved in a liquid environment, such as phosphate buffer solution, saline, or other simulated body fluids. Once such biological materials are out of the environment of preservation liquid used for preservation for too long, there will be a dehydration phenomenon, resulting in irreversible changes in structure and properties, which may cause failure of material or product. Therefore, processing and preservation of such biological materials are required to be performed in an environment of preservation liquid.

However, since most preservation liquids contain water or other volatile organic solvents, there is a limitation that the biological materials cannot be out of the environment of the aqueous preservation liquid for too long. This brings lots of inconvenience for the processing and storage of the biological materials.

For example, the time that the biological material out of the preservation liquid needs to be strictly limited in all processing, so as to prevent irreversible materials damage caused by excessive volatilization of the preservation liquid contained in the biological materials. The sterilization ways for these materials are often limited too, usually only chemical liquid sterilization, radiation sterilization, et al., can be applied. In addition, packaging for related product of such materials usually includes packaging the product itself and the preservation liquid, therefore the packaging process is relatively complicated, and it is more difficult to maintain sterility of the product.

As a common implanted material, the decellularized collagenous tissue has been widely applied in the medical field. The decellularized collagenous tissues described above are human- or animal source biomatrix materials that have been decellularized to remove antigenicity thereof and mainly consisted of collagenous fibers, such as pericardium, valves, intestinal mucosa, dermal, ligaments, tendons, blood vessels, sclera. The decellularized collagenous tissue may contain or partially contain components of elastic fiber, proteoglycans, glycoproteins, hyaluronic acid et al., in addition to the collagenous fibers. The methods for decellularization as described above may be common physical methods (for example, lyophilization method) and chemical methods (for example, method involving surfactants, acidic or basic treatment, and a chelating agent), and other methods that can remove cells from the tissue.

The decellularized collagenous tissues may be used as main sources or components of biological patches, artificial dura mater, bioprosthetic valves, transcatheter valves and other medical devices. In the processing of decellularized collagenous tissue, one common method is crosslinking the decellularized collagenous tissue by using aldehyde compounds, such that the decellularized collagenous tissue has a good stability after being implanted.

Decellularized collagenous tissues, or medical devices containing the decellularized collagenous tissue, such as bioprosthetic valve and transcatheter valve, are usually need to be sterilized and preserved in an aqueous solution containing aldehyde in order to maintain the sterility of the materials. In the clinical use, the biological tissue materials or medical devices containing such biological tissue materials need to be taken out of the aldehyde-containing preservation liquid, and rinsed thoroughly, so as to reduce residual aldehyde in the biological tissue materials, which may cause the tissue inflammatory response. Therefore, conventional liquid preservation methods for such biological materials and device have increased procedures and safety risks in the clinical uses and they tend to be less convenient. In the case of transcatheter valve which contains a valve and a delivery system, as the valve contains collagenous materials, which would be dehydrated in the absence of aqueous environment, therefore the valve needs to be packaged and stored separately, rather than assembled with the delivery system. This type of conventional storage causes inconvenience. The valve and the delivery system need to be assembled by a physician before the clinical use instead of being assembled before leaving the factory, which not only brings inconvenience in use but also makes the quality control of assembly processing more difficult.

Therefore, the preservation of biological materials described above in a "dry" environment after being taken out from the aqueous preservation liquid is significant in the field of scientific research and related industry.

DETAILED DESCRIPTION

The present invention provides a method for preservation processing a decellularized collagenous tissue, with this method the decellularized collagenous tissue can be effectively preserved in a non-liquid environment without irreversible deformation or degeneration caused by volatilization of liquid in the decellularized collagenous tissue when the decellularized collagenous tissue is taken out of liquid environment, which will allow the decellularized collagenous tissue being processed, sterilized, preserved and used et al in a non-liquid environment.

The present invention also provides a method for preservation processing an artificial heart valve comprising the decellularized collagenous tissue. With this method, the deformation of the biological tissue in the artificial heart valve that generally happened when it is preserved in a non-liquid environment can be effectively avoided. The process, sterilization, preservation and utilization of the decellularized collagenous tissue a non-liquid environment will be permitted.

The present invention also provides a decellularized collagenous tissue, which can be preserved in a non-liquid environment, and can be conveniently processed, sterilized, preserved, used and so on.

The present invention also provides an artificial heart valve containing the decellularized collagenous tissue, which can be preserved in a non-liquid environment, and can be conveniently processed, sterilized, preserved, used and so on.

The present invention also provides a use of the artificial heart valve containing the decellularized collagenous tissue for being directly implanted into human body.

The present invention also provides a medical device containing the decellularized collagenous tissues, such as biological patches, artificial dura mater, and so on.

The present invention provides a method for processing the decellularized collagenous tissue, which comprises immersing the decellularized collagenous tissue in the preservation liquid comprising an ionic liquid for a proper time so that the decellularized collagenous tissue will remain its size in a non-liquid environment.

The present invention provides a method for preservation processing the artificial heart valve containing the decellularized collagenous tissue, which includes immersing the artificial heart valve in the preservation liquid comprising an ionic liquid for a proper time until the size of the decellularized collagenous tissue remains stable in a non-liquid environment.

In the present invention, "preservation process" means immersing the tissue in a preservation liquid containing an ionic liquid until size of the tissue remains stable in a non-liquid environment; "a non-liquid environment" means the decellularized collagenous tissue or the artificial heart valve containing the decellularized collagenous tissue is not immersed in liquid or there is no excessive liquid on the material surface, the environment also can be an atmospheric environment that without any liquid; "dry storage" means the tissue is not immersed in fluid or there is no excessive amount of fluid on the surface of the tissue. The tissue can be stored either in an air tight environment or not. For example, when the tissue is preservation processed and taken out from the preservation liquid containing an ionic liquid, then the excessive preservation liquid adhere on the surface is removed, the tissue now is in a dry storage state; "size remains stable" should be understood as the size of the decellularized collagenous tissue after being processed by the above described preservation liquid remains substantially unchanged in each dimension, or may have some slight changes that are still within the acceptable rang in the art, and should not be understood as an absolute constant size; "a proper time" should be understood as a period of time that required for immersing the decellularized collagenous tissue and the artificial heart valve containing the decellularized collagenous tissue in the preservation liquid until the size of the decellularized collagenous tissue remains stable. This can be determined by the properties of biological materials and ionic liquids, that is, the time for immersing is certain after biological materials and ionic liquids are determined, which is an objective data.

Generally, if biological materials preserved in an aqueous solution are out of the liquid environment for too long, changes would appear in appearance, size or shape due to dehydration of the biological materials. For example, the materials will appear changed color, shrinked size, and so on. Once these phenomena appear in materials, it indicates that the structure inside the materials has changed due to the evaporation of the preservation liquid, which causes the material to degenerate. After being processed by the method provided in the present invention, damage of the biological material caused by volatilization of the preservation liquid in the biological material can be effectively avoided, and the biological material can be conveniently processed, sterilized, stored and used.

The preservation liquid containing an ionic liquid will gradually penetrates and immerges into the decellularized collagenous tissue after the decellularized collagenous tissue is completely immersed in the preservation liquid. The preservation liquid containing an ionic liquid will replace all or part of the intrinsic liquids contained in the decellularized collagenous tissue. The intrinsic liquids in collagen tissue may comprise water or aqueous solution of water and one or more than two of buffer solution, simulated body fluid, aldehydes, monohydric-alcohols and polyhydric-alcohols. The person skilled in the art should understand that immersing the decellularized collagenous tissue in the preservation liquid is essentially to replace the intrinsic liquids in the decellularized collagenous tissue with the preservation liquid containing an ionic liquid.

The time that required for preservation processing the decellularized collagenous tissue in the preservation liquid containing an ionic liquid varies depending on different types and sizes of decellularized collagenous tissue to be processed. In general, the time must be over 10 minutes, and the longer the time is, the better the effect will be. And the resulting processed decellularized collagenous tissue should be able to maintain size stability during the subsequent processing and preservation procedures after being taken out from the preservation liquid, that is, the size of the resulting processed decellularized collagenous tissue will not change due to the evaporation of the preservation liquid in the decellularized collagenous tissue.

The resulting processed decellularized collagenous tissue can be directly used for subsequent processing after being taken out from the preservation liquid and removing the excessive preservation liquid on a surface thereof. Now the tissue is in the "dry storage" state. The method for removing the excessive preservation liquid on the surface of the resulting processed decellularized collagenous tissue may be a simple wiping, or any other methods that may effectively remove the surface liquid of the collagenous tissue. In other words, the resulting processed decellularized collagenous tissue which is in the dry storage state can be stored for a long time or can be subjected to other processes such as cutting and packaging under a non-liquid environment condition.

The ionic liquid used in the present invention is commercially available or can be self-prepared by known methods, for example, a method for preparing related ionic liquids is disclosed in patent application CN1651089A.

According to the method provided by the present invention, the preservation liquid contains at least 10%-100% of the ionic liquid. Increasing the content of ionic liquid would be beneficial for the size stability and long-term preservation of the processed decellularized collagenous tissue. For example, the preservation liquid may contain 50%-100% of the ionic liquid.

According to the method provided by the present invention, the preservation liquid may also contain one or more of other components such as water, water-soluble alcohols, water soluble carbohydrates and water-soluble rubber and so on, in addition to the ionic liquid. The water-soluble alcohols may be monohydric-alcohols or polyhydric-alcohols, preferably alcohols containing 1 to 4 carbon atoms. A polymer of the water-soluble alcohols monomers can also be used. For example, water-soluble alcohols may be ethanol, glycerol, ethylene glycol, isopropyl alcohol, acetone, polyethylene oxide, and so on.

According to the method provided by the present invention, the ionic liquid can be miscible with water, which would be beneficial for obtaining a homogeneous preservation liquid.

According to the method provided by the present invention, the ionic liquid is biocompatible. The ionic liquid that is safe and non-toxic to organisms does not produce adverse clinical responses, and the processed biological materials by this ionic liquid can be directly used for implantation without adding a rinsing procedure. Of course, when the ionic liquid contained in the preservation liquid of the processed biological materials is not suitable for entering the organisms (for example, when the ionic liquid is not biocompatible), the ionic liquid is washed off by a rinsing procedure (for example, rinsing with saline or buffer solution) prior to the implantation.

According to the method provided by the present invention, the ionic liquid may be a quaternary ammonium salt ionic liquid and an alkyl imidazolium salt ionic liquid.

According to the method provided by the present invention, the ionic liquid may be a water-miscible quaternary ammonium salt ionic liquid, a water-soluble alkyl imidazolium salt ionic liquid and so on.

According to the method provided by the present invention, the quaternary ammonium salt ionic liquids consist of choline salts and complexing agents, and the choline salts include one or more substances of choline, choline chloride, choline fluoride, choline nitrate, choline hydroxide, choline bicarbonate, acetyl choline, phosphorylcholine, choline butyryl, benzoyl choline or phosphatidylcholine, and the complexing agents include one or more substances of urea, ethylene glycol, glycerol, citric acid, malonic acid, amino acids, lactic acid, a fatty acid having a alkyl group with 1-30 carbon atoms and derivatives thereof containing a hydroxyl group or a carboxyl group. For example, choline chloride/urea, choline chloride/glycerol, choline hydroxide/glycine ionic liquids and so on.

According to the method provided by the present invention, the alkyl imidazolium salt ionic liquids consist of a cation of alkyl imidazolium salt having 1-8 carbon atoms or derivatives thereof containing a hydroxyl group or a carboxyl group, and an anion of fatty acid salt having a alkyl group with 1-30 carbon atoms or derivatives thereof containing a hydroxyl group or a carboxyl group. For example, acetic acid 1-methyl-3-ethyl imidazole and so on.

It is found according to the inventors' research that immersing the biological material in the preservation liquid containing ionic liquids is a process that the preservation liquid containing ionic liquids enters the biological tissue to replace the internal liquids (i.e. intrinsic liquids) of biological tissue, and a certain amount of the entered ionic liquid has an effect of maintaining the size of biological material unchanged. According to the method provided by the present invention, the ionic liquid in the decellularized collagenous tissue processed by the preservation liquid containing ionic liquid accounts for at least 10% by weight of the total amount of liquid components (i.e. the preservation liquid and the intrinsic liquids) in the decellularized collagenous tissue. When all the intrinsic liquids in the decellularized collagenous tissue are replaced by the preservation liquid, the liquid components will be the preservation liquid. According to the method provided by the present invention, the preservation liquid may contain one or more ionic liquids.

Generally, water-miscible ionic liquid is beneficial to achieve the replacement of the intrinsic preservation liquid in the tissue with the preservation liquid containing ionic liquid, and also benefit for the material washing before implanting, and therefore the ionic liquid is preferable miscible with water. But it does not exclude the possibility of using non-water-miscible ionic liquid, especially when using in combination with other preservation liquids.

According to the method provided by the present invention, wherein the decellularized collagenous tissue and the artificial heart valve containing decellularized collagenous tissue being processed by the preservation liquid containing ionic liquid can be preserved in very normal environments such as at a environment temperature from −5 to 45° C., a relative humidity of 5-95%, or even lower temperatures, for example, −10° C. for a long time, the temperature is related to the freezing point of the preservation liquid containing ionic liquid in the tissue.

It is necessary to point out that temperature and humidity of the preservation environment may influence the water content in the tissue materials, especially when the dry storage tissue is in a non-sealed condition.

According to the method provided by the present invention, after the decellularized collagenous tissue or artificial heart valve containing decellularized collagenous tissue is taken out from the preservation liquid, removing the excessive preservation liquid adhered on the surface thereof, packaging and sterilizing the decellularized collagenous tissue or artificial heart valve, then the decellularized collagenous tissue or artificial heart valve can be directly stored and transported. The method of the present invention can also be used for preservation processing a sterilized decellularized collagenous tissue or a sterilized artificial heart valve containing the decellularized collagenous tissue, and of course, the preservation processing should be performed under sterilized conditions.

In general, biological materials those have to be stored in liquid environments or medical devices containing these materials are usually sterilized by chemical liquid or radiation. They cannot be sterilized by ethylene oxide. However, through the method of preservation processing provided by the present invention, the decellularized collagenous tissue or artificial heart valve containing the decellularized collagenous tissue will be preservation processed in the preservation liquid containing ionic liquid, the tissue or artificial heart valve containing such collagenous tissue can be sterilized by ethylene oxide. This sterilization method by ethylene oxide is not possible for biological materials those stored in liquid environment. Of course, the person skilled in the art should understand that the sterilization herein can also be other conventional sterilization means, for example: radiation sterilization.

Therefore, according to the method provided by the present invention, the first sterilization method of the decellularized collagenous tissue or artificial heart valve containing the decellularized collagenous tissue includes the following procedures: (1) the preservation liquid and the decellularized collagenous tissue or artificial heart valve containing the decellularized collagenous tissue are all sterilized before being preserved in the preservation liquid containing ionic liquids; (2) then conducting preservation processing on the decellularized collagenous tissue or the artificial heart valve containing the decellularized collagenous tissue in the preservation liquid under a sterilized environment; (3) further processing and packaging the decellularized collagenous tissue or the artificial heart valve under a sterilized environment.

According to the method provided by the present invention, the second sterilization method of the decellularized collagenous tissue or artificial heart valve containing decellularized collagenous tissue includes the following steps: (1) first conducting preservation processing on the decellularized collagenous tissue or artificial heart valve containing decellularized collagenous tissue in the preservation liquid; (2) then sterilizing the decellularized collagenous tissue or artificial heart valve. The decellularized collagenous tissue or artificial heart valve containing decellularized collagenous tissue or preservation liquid in step (1) may also be pre-sterilized.

According to the method provided by the present invention, as for the transcatheter valve, the decellularized collagenous tissue may be processed by the preservation liquid containing ionic liquid in any suitable process before assembling the valve component containing decellularized collagenous tissue and the delivery system, such that the decellularized collagenous tissue maintains its size stability after being taken out of the liquid environment, and then the valve component and the delivery system are assembled, packaged and sterilized.

According to the method provided by the present invention, wherein the sterilization is ethylene oxide sterilization or radiation sterilization.

According to the method provided by the present invention, the decellularized collagenous tissue may include pericardium, valves, brain dura mater, intestinal mucosa, dermis, ligaments, tendons, blood vessels, and sclera after being decellularized processed.

The present invention also provides a method for processing the decellularized collagenous tissue, and the artificial heart valve containing the decellularized collagenous tissue, such as transcatheter valve and bioprosthetic valve. The artificial heart valve containing the decellularized collagenous tissue can be preservation processed into an implantable device for clinical uses, either used with rinsing or directly without rinsing.

The present invention also provides a method for preserving the decellularized collagenous tissue or the artificial heart valve containing the decellularized collagenous tissue. This method includes immersing the decellularized collagenous tissue or the artificial heart valve containing the decellularized collagenous tissue in the preservation liquid containing ionic liquid until the size of the decellularized collagenous tissue remains stable in a non-liquid environment, taking the decellularized collagenous tissue or the artificial heart valve containing the decellularized collagenous tissue out of the preservation liquid, removing the excessive preservation liquid adhered on the surface thereof, and further processing the decellularized collagenous tissue and the artificial heart valve.

According to the method provided by the present invention, the further processing of the transcatheter valve also includes assembling the transcatheter valve with the delivery system. The further processing of the decellularized collagenous tissue includes cutting, shaping, sewing et al.

According to the method provided by the present invention, the further processing the biological materials such as the decellularized collagenous tissue or the artificial heart valve containing the decellularized collagenous tissue after being taken out from the preservation liquid also comprises sterilizing the biological materials, or sterilizing the biological materials after packaging.

According to the method provided by the present invention, the sterilization is ethylene oxide sterilization or radiation sterilization.

According to the method provided by the present invention, the packaging that chosen for packing the processed biological materials can be ones that only block microorganism but not the air, for example, TYVEK® kind of packaging, or ones that not only can block microorganism but also the air and achieve completely sealing of the processed biological materials.

The implementation of the present invention has at least the following advantages:

1. The method provided by the present invention comprises immersing the decellularized collagenous tissue in a preservation liquid containing ionic liquid, during which there is no need to worry about the structure or property damage of the decellularized collagenous tissue caused by dehydration in the non-liquid environment, which makes it simple to process, store and use the biological materials containing the decellularized collagenous tissue. It also makes it possible to assemble the valve-delivery system in factory and make it ready to use, instead of requiring the physician to assemble the valve-delivery system in operation house.

2. The method provided by the present invention can eliminate detrimental impacts caused by aldehyde residue in conventional preservation liquid, which may still exist after rinsing the decellularized collagenous tissue before surgery, on the properties of the decellularized collagenous tissue, and reduce the possible adverse effects occurred after implanting the decellularized collagenous tissue in the body.

3. The decellularized collagenous tissue that processed by the preservation liquid containing ionic liquid provided by the present invention make it possible to sterilize this tissue or devices containing such tissue. It provides more choices and makes the sterilization more convenient and effective.

4. The decellularized collagenous tissue that processed by the preservation liquid containing ionic liquid provided by the present invention maintains its required structure and properties, such as mechanical properties and biological properties.

5. The present invention makes the tissue materials more tolerant to the preservation environment and form of package is much simple.

6. Dry storage provides an optimal choice for the design and application of the tissue contenting medical device products.

DESCRIPTION OF EMBODIMENTS

Generally, all of the biological materials contain a certain amount of liquid, which may be water, or an aqueous solution of one or more substances of water and buffer solution, simulated body fluid and aldehydes, monohydric- or polyhydric alcohols, for example, the aqueous solution in decellularized bovine heart tissue may contain 70-90% of water. After the decellularized collagenous tissue is completely immersed in the preservation liquid, the preservation liquid containing an ionic liquid will gradually penetrates and immerges into the decellularized collagenous tissue to replace all or part of the intrinsic liquids contained in the decellularized collagenous tissue.

The present invention will be more adequately described in the following with the reference to the embodiments in the present invention. However, the present invention may be embodied in many different forms and should not be understood as limited to the embodiments stated herein.

Embodiment 1

The decellularized bovine pericardium tissue samples (size: 5 cm×5 cm, thickness: 0.5 mm), which was cut by laser and crosslinking-fixed with glutaraldehyde, were taken out of the phosphate buffer solution, and put into 100 g transparent choline chloride/urea ionic liquid (the preparation method thereof can be referenced to AP Abbott et al., Chem. Commun, 2003, 7071), the molar ratio of choline chloride and urea that used to form the ionic liquid was 1:2. It could be observed that transparency of the bovine pericardium tissue is gradually improved with the increased time of immersing the tissue in the preservation liquid containing the ionic liquid, and the ionic liquid gradually penetrates and immerges into the bovine pericardium tissue. Immersing time was generally more than 10 min, for example, after being immersed for 1 hour, the bovine pericardium tissue was taken out, and removing the excess liquid adhered on the surface of the tissue, and measuring the size thereof. The tissue was then stored in a non-sealed environment for 24 months under room temperature, repeatedly measuring the size and comparing the size change during deposition. The results were shown in Table 1.

TABLE 1

| Time point | Length, mm | Width, mm | Thickness, mm |
|---|---|---|---|
| when the sample was just taken out of the ionic liquid | 50 | 50 | 0.49 |
| 24 months after storing the sample in a non-liquid environment | 50 | 50 | 0.49 |

Wherein the thickness was measured by selecting five fixed points on the decellularized tissue, and taking an average value of thickness measured at the five points.

When comparing the tissue having the ionic liquid accounts for at least 10% by weight of the liquid components in the tissue to the tissue that had not been processed by the preservation liquid containing ionic liquid, the size change rate of the former tissue significantly slows down under normal temperature condition, and a higher weight percentage of ionic liquid to liquid components in the tissue brings a better size stability of the tissue. The processing time (including the repeated times of the processing) or processing conditions (such as the required weight percentage of ionic liquid to the liquid components in the tissue) can be adjusted and determined according to the required maintain time of the size stability, for example, when there was a need of long-term preservation of the tissue in a non-liquid environment such as several months, several years or even longer, it is preferred that ionic liquid accounts for 50-100% by weight of the liquid components in the tissue.

In Embodiment 1, when the ionic liquid was used to preserve one piece of decellularized bovine pericardium tissue, the weight percentage of the ionic liquid to the liquid components in the tissue was 85-98%, and this specific value was related to the amount of phosphate buffer solution that the pericardium piece has brought into the ionic liquid.

The mechanical properties of the bovine pericardium in Embodiment 1 were tested, the pericardium material was taken out of phosphate buffer solution before being processed by the preservation liquid containing the ionic liquid, and its tensile strength and elongation at break were respectively 13.1±7.5 MPa, and 27.2±8.4%; after the preservation processing, the pericardium material was deposited under room temperature for 24 months, and after being washed to remove the preservation liquid containing ionic liquid, the tensile strength and elongation at break of the pericardium material were respectively 12.7±5.8 MPa, 30.1±9.7%. Thus, the mechanical properties of the pericardium material that processed by the method provided by the present invention did not significantly change even after a long-time storage.

Embodiment 2

The decellularized bovine pericardium tissue (size: 5 cm×5 cm, thickness: 0.5 mm), which was crosslinking-fixed with glutaraldehyde and processed by anti-calcification, was put into 100 g of transparent choline chloride/urea ionic liquid, after being immersed for 1 hour, the decellularized bovine pericardium tissue was taken out, removing the excess ionic liquid adhered on surface of the tissue, then shaping the tissue; or the bovine pericardium tissue may be preserved in the choline chloride/urea ionic liquid for a long time, and can be taken out and processed into required shape when in use.

The bovine pericardium tissue can be cut by laser into the required shape and size of biological patches, and packaged and sealed in a two-layers sterile barrier consisted of a PETG box and a Tyvek cover, then sterilized with ethylene oxide (the sterilizing temperature is 37° C., other parameters are all conventional setting).

The size of the bovine pericardium tissue was measured with method described above, and it remains substantially stable in a non-liquid environment.

Sterility testing was performed to the bovine pericardium tissue, the result was sterile. It illustrates that ethylene oxide sterilization method was effective to the bovine pericardium tissue containing ionic liquid. In the following, biocompatibility of the processed bovine pericardial tissue was evaluated by subcutaneously implanting the biological patch produced from the processed bovine pericardial tissue into mice. The biological patches for implanting experiments were divided into the following three groups:

Rinsed group: The biological patch, which was processed by the ionic liquid and sterilized, was cut into a small piece of 1 cm×1cm, and rinsed in 100 ml sterile saline for three times, 10 seconds each time prior to implantation.

Direct implantation group: the biological patch, which was processed by the ionic liquid and sterilized, was implanted subcutaneously into mice without being rinsed;

Control group: the biological patch produced from the bovine pericardium tissue, which was cut into size of 1 cm×1 cm, was chemically sterilized with glutaraldehyde, and preserved in a phosphate buffer solution containing 0.6 wt % of glutaraldehyde, and rinsed by the same way as described in the rinsed group before being implanted.

Samples from three groups were implanted subcutaneously into mice to evaluate the biocompatibility of the patches, the results were shown in Table 2.

TABLE 2

| Sample Groups | Processing methods | Sterilization methods | Rinsed before implantation | Inflammatory response of mice after implantation |
|---|---|---|---|---|
| Rinsed group | Choline chloride/urea ionic liquid | Ethylene oxide sterilization | Rinsed | Lower |
| Direct implantation group | Choline chloride/urea ionic liquid | Ethylene oxide sterilization | Non-rinsed | Lower |
| Control group | Phosphate Buffer solution containing 0.6 wt % glutaraldehyde | Chemical sterilization | Rinsed | Higher |

The experiment results indicated that inflammatory response of mice after implantation of patch samples from two groups processed by the ionic liquid (Rinsed group and Direct implantation group) was significantly lower than that of the control group (processed with conventional aldehyde sterilization and storage), which demonstrates that the biocompatibility of patches processed with ionic liquid was better than that of patches processed with phosphate buffer solution of glutaraldehyde, which could be because of the patches processed with the ionic liquid has reduced amount of glutaraldehyde in the patch tissue than the patches from Control group, and glutaraldehyde residual was usually considered as one important reason of causing inflammatory response.

On the other hand, inflammatory response of mice after implantation of patch samples from rinsed group and direct implantation group was lower, which illustrates that the choline chloride/urea ionic liquid used had a good biocompatibility in mice.

The processing method of the embodiment allows the decellularized collagenous tissue can be conveniently mechanical-processed even out of the conventional preservation liquid, and in the process there was no need to worry about the material degeneration caused by evaporation of the aqueous preservation liquid, therefore after taking out the material that conducted preservation processing from the preservation liquid containing ionic liquid, removing the excessive preservation liquid on surface thereof, it can be cut and sewed in the non-liquid environment to produce bioprosthetic valves or transcatheteral valves that do not need to be preserved in the preservation liquid, and the bioprosthetic valves or transcatheteral valves can be sterilized with ethylene oxide after being packaged in the non-liquid environment, which makes it simple to process, store and use the biological materials containing the decellularized collagenous tissue. It also makes it possible to assemble the valve-delivery system in factory and make it ready to use, instead of requiring the physician to assemble the valve-delivery system in operation house.

Embodiment 3

The porcine pericardium tissue (size: 5 cm×5 cm) processed by anti-calcification was put into 105 g of preservation liquid that contained 20 g of choline chloride/glycerin ionic liquid (the molar ratio of choline chloride and glycerin that used to form the ionic liquid was 1:2), 80 g of choline chloride/urea (molar ratio 1:2) ionic liquid, and 2 g of ethanol, 2 g of glycerin, 1 g of water. After being completely immersed for 2 hours, the porcine pericardium tissue was taken out and measured by the same method as described in the above embodiment. The size of the porcine pericardium tissue in the non-liquid environment remained substantially stable and the mechanical properties thereof also had not significantly changed. After removing the excessive preservation liquid adhered on the surface, the porcine pericardium tissue was cut into a valve leaflets shape, then the valve leaflets and a transcatheter valve frame were manually sewed together to produce a transcatheter valve. The transcatheter valve was assembled with the delivery system, then packaged by TYVEK® paper & plastics package, and sterilized by ethylene oxide.

In this embodiment, since the porcine pericardium tissue used for preparing valves was infiltrated by non-volatile preservation liquid, therefore it can be processed in a non-liquid environment after being taken out of the preservation liquid, and there is no need to worry about the material degeneration caused by evaporation of the preservation liquid. Therefore, the transcatheter valve may be packaged and sterilized with ethylene oxide after being assembled with the delivery system, so as to avoid the problem that is caused by the fact that when using the conventional preservation liquid to process the transcatheter valve, the press-fitting processing usually needs to be performed before the implantation of the transcatheter valve.

Embodiment 4

2.5 cm of decellularized processed canine carotid artery was immersed in 50 ml of acetate 1-methyl-3-ethyl imidazole ionic liquid ([Emim] Ac) so to be preserved, and the decellularized processed canine carotid artery can be taken out when in use. The method for preparing the ionic liquid can be referred to the relevant literatures (for example, Huang Yinrong et al., Preparation of 1-methyl-3-ethyl-imidazole acetate and measurement of density, conductivity, Xi'an Engineering University, 2011, Vol 25(5), pp. 689-692).

The canine carotid artery preserved by the method of this embodiment can be used without rinsing, and can be directly implanted into body, which is convenient for use.

The size, mechanical properties of the decellularized canine carotid artery in the non-liquid environment were measured by the same method as described in the above embodiment, and the size was substantially stable, the mechanical properties also did not have significantly change.

Embodiment 5

According to the method of Embodiment 3, 20 g of choline chloride/glycerol (molar ratio of 1:2) ionic liquid and 80 g of choline chloride/ethylene glycol (molar ratio of 1:2) ionic liquid were prepared respectively, and after mixing these two ionic liquids, 2 g of glycerol, 2 g of ethanol and 1 g of water were added therein to prepare a 105 g of preservation liquid.

The decellularized porcine dermis tissue was put into the prepared preservation liquid for extended storage. And it can be taken out and removing the excessive preservation liquid on the surface (in the "dry storage" state) thereof, packaged, sterilized by radiation when required.

The size, mechanical properties of the decellularized porcine dermis tissue in the non-liquid environment were measured by the same method as described in the above embodiment, and the size was substantially stable, the mechanical properties also did not have significantly change.

Finally, it should be noted that: each embodiment above is only used for illustrating the technical solutions of the present invention, but not limited to it; although the present invention has been illustrated in detail with the reference to the foregoing embodiments, the person skilled in the art should understand that: they still can modify the technical solutions described in the foregoing embodiments, or equivalently replace partly or all technical features; while these modifications or replacements do not make the essence of corresponding technical solutions depart from the range of technical solutions of each embodiment of the present invention.

What is claimed is:

1. A method of preserving an implantable medical device or its components, comprising the steps of:
immersing the device or its components in a preservation liquid containing a biocompatible ionic liquid wherein the ionic liquid is one or a combination of two or more of quaternary ammonium salt ionic liquids until a weight percentage of the ionic liquid versus total liquid in the device or its components is at least 10%,
taking the device or its components out of the preservation liquid to remove excess preservation liquid, and
sterilizing the device before implantation, wherein the device comprises decellularized biological tissue that maintains required properties for implantation after sterilizing, further wherein a required property is size stability and wherein the quaternary ammonium salt ionic liquids consist of choline salts and complexing agents, and the choline salts comprise one or more substances of choline, choline chloride, choline fluoride, choline nitrate, choline hydroxide, choline bicarbonate, acetyl choline, phosphorylcholine, choline butyryl, benzoyl choline or phosphatidylcholine, and the complexing agents comprise one or more substances of urea, ethylene glycol, glycerol, citric acid, malonic acid, amino acids, lactic acid, fatty acids having a alkyl group with 1-30 carbon atoms and derivatives thereof containing a hydroxyl group or a carboxyl group.

2. The method according to claim 1, wherein the decellularized tissue comprises decellularized pericardium, decellularized valves, decellularized brain dura mater, decellularized intestinal mucosa, decellularized dermis, decellularized ligaments, decellularized tendons, decellularized blood vessels, and decellularized sclera.

3. The method according to claim 1, wherein the device is a decellularized heart valve.

4. The method according to claim 1, wherein the device comprises a bioprosthetic valve or a transcatheter valve.

* * * * *